United States Patent [19]

Kosóczky et al.

[11] 4,419,355
[45] Dec. 6, 1983

[54] CONDENSED AS-TRIAZINE DERIVATIVES AND METHOD OF USING THE SAME

[75] Inventors: Ibolya Kosóczky; Éva Toncsev, née Rávasz; Pál Benkő; László Pallos; Lujza Petócz; Sándor Bátori; György Hajós; András Messmer; Katalin Grasser, all of Budapest, Hungary

[73] Assignee: Egyt Gyogyszervegyeszeti Gyar, Budapest, Hungary

[21] Appl. No.: 283,971

[22] Filed: Jul. 16, 1981

[30] Foreign Application Priority Data

Jul. 18, 1980 [HU] Hungary .............................. 1798/80

[51] Int. Cl.³ .................... C07D 253/08; A61K 31/53
[52] U.S. Cl. ...................................... 424/249; 544/183
[58] Field of Search ......................... 544/183; 424/249

[56] References Cited

U.S. PATENT DOCUMENTS

4,080,192  3/1978  Wolf .................................... 544/183

OTHER PUBLICATIONS

Japan—Chemistry Letters, pp. 413-414, 1976, published by Chemical Society of Japan, Synthesis and Characterization of 1-Imidoyliminopyridinium N-ylides; Akikazu Kakehi et al.

Primary Examiner—John M. Ford
Attorney, Agent, or Firm—Karl F. Ross; Herbert Dubno

[57] ABSTRACT

The invention relates to new condensed as-triazine derivatives of the general formula (I)

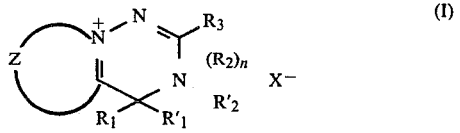

wherein
Z represents a buta-1,3-dienyl group or a group of the formula (a), (b), (c) or (d)

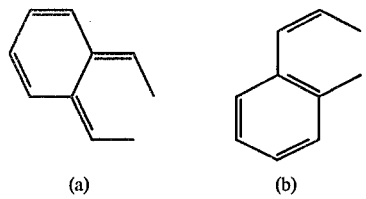

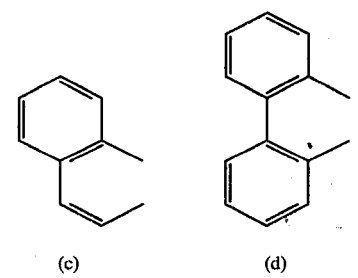

$R_1$ denotes a $C_{1-10}$ alkyl group, an oxo group or a $C_{6-10}$ aryl or $C_{6-10}$ aryl-($C_{1-3}$ alkyl) group optionally substituted by one or more identical or different substituents selected from the group consisting of amino, nitro, $C_{1-6}$ alkyl, $C_{1-6}$ alkoxy, hydroxy and halogen,
$R_2$ stands for hydrogen, $C_{1-10}$ alkyl or amino,
$R_3$ represents hydrogen, $C_{1-10}$ alkyl or $C_{6-10}$ aryl or $C_{6-10}$ aryl-($C_{1-3}$ alkyl) optionally substituted by one or more identical or different substituents selected from the group consisting of nitro, amino, $C_{1-6}$ alkyl, $C_{1-6}$ alkoxy, hydroxy and halogen,
$X^-$ denotes an anion, and
n is 0 or 1, with the proviso that if n is O, $R_1$ is other than an oxo group and $R_1'$ and $R_2'$ form together a double bond, and with the further provisos that if n is 1, $R_1$ represents an oxo group and the symbols $R_1'$ and $R_2'$ are not present, and if Z is a buta-1,3-dienyl group and $R_1$ denotes an oxo group, $R_3$ is other than unsubstituted phenyl.

The new compounds of the general formula (I) can be prepared by cyclizing the compounds of the general formula (II) or (V), wherein $R_1$, Z, $R_3$ and $X^-$ have the above defined meanings, $R_4$ is a leaving group and $R_7$ represents hydrogen or $C_{1-10}$ alkyl.

The new compounds of the general formula (I) possess a valuable antidepressant effect and can advantageously be used in the therapy.

10 Claims, No Drawings

CONDENSED AS-TRIAZINE DERIVATIVES AND METHOD OF USING THE SAME

The invention relates to new condensed as-triazine derivatives, a process for the preparation thereof and pharmaceutical compositions containing the same.

1-(4H)-oxo-pyrido-[2,1-f]-as-triazinium salts substituted by a phenyl group in position 3 are described in Chem. Lett. (1976), 5 pp. 413–414 and J. Org. Chem. 42, (3), pp. 443–448 (1977). 1-Methoxy-3-phenyl-pyrido[2,1-f]-as-triazinium bromides substituted by four methoxycarbonyl groups on the phenyl ring are provided in Liebigs Ann. Chem. (1977), pp. 1421–1428 and 1718–1724. No biological activity was attributed to these compounds.

According to a feature of the present invention there are provided condensed as-triazine derivatives of the formula (I)

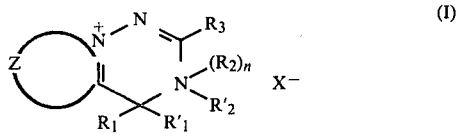

wherein
Z represents a buta-1,3-dienyl group or a group of the formula (a), (b), (c) or (d)

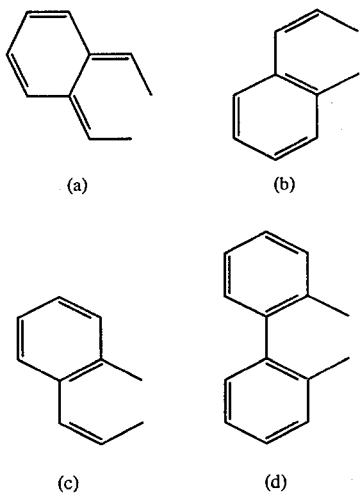

$R_1$ is $C_{1-10}$ alkyl group, an oxo group or $C_{6-10}$ aryl or $C_{6-10}$ aryl-($C_{1-3}$ alkyl)optionally substituted by one or more identical or different substituents selected from the group consisting of nitro, amino, $C_{1-6}$ alkyl, $C_{1-6}$ alkoxy, hydroxy and halogen, $R_2$ is hydrogen, $C_{1-10}$ alkyl or amino, $R_3$ is hydrogen, $C_{1-10}$ alkyl or $C_{6-10}$ aryl or $C_{6-10}$ aryl-($C_{1-3}$ alkyl)optionally substituted by one or more identical or different substituents selected from the group consisting of nitro, amino, $C_{1-6}$ alkyl, $C_{1-6}$ alkoxy, hydroxy and halogen, $X^-$ denotes an anion, and
n is 0 or 1,
but when n is 0, $R_1$ is other than an oxo group and $R_1'$ and $R_2'$ form together a double bond, and when n is 1, $R_1$ represents an oxo group and the symbols $R_1'$ and $R_2'$ are not present, and when Z is a buta-1,3-dienyl group and $R_1$ denotes an oxo group, $R_3$ is other than unsubstituted phenyl.

The term "alkyl" refers to straight-chained or branched saturated aliphatic hydrocarbons (e.g. methyl, ethyl, n-propyl, isopropyl, n-butyl, tert.-butyl). The term "alkoxy" relates to alkylether groups containing the above defined alkyl groups (e.g. methoxy, ethoxy, n-propoxy, isopropoxy). The "$C_{6-10}$ aryl" denotes phenyl and naphthyl groups. Preferred representatives of the $C_{6-10}$ aryl-($C_{1-3}$ alkyl) groups are benzyl, β-phenylethyl, diphenyl-methyl and β,β-diphenyl-ethyl. The aryl ring of the above defined aryl and aralkyl groups optionally contains one or more identical or different substituents. Preferred representatives of the said substituents are the nitro, amino, $C_{1-6}$ alkyl, $C_{1-6}$ alkoxy and hydroxy groups and halogen. The term "halogen" encompasses fluorine, chlorine, bromine and iodine. $X^-$ represents preferably a halide (e.g. chloride, bromide or iodide), perchlorate, p-toluene-sulfonate or methanesulfonate ion. X may stand for any pharmaceutically acceptable anion.

Preferred representatives of the compounds of the formula (I) are the compounds in which $R_1$ is phenyl, halophenyl or oxo group, $R_2$ is hydrogen or $C_{1-4}$ alkyl, $R_3$ is hydrogen or $C_{1-4}$ alkyl, Z is a buta-1,3-dienyl group or a group of the formula (a) or (c) and $X^-$ represents a chloride, perchlorate, bromide or p-toluenesulfonate anion, and n is 0 or 1, and when n is 0, $R_1$ is other than an oxo group, and $R_1'$ and $R_2'$ form together a double bond, and when n is 1, $R_1$ represents an oxo group and $R_1'$ and $R_2'$ are not present.

Particularly preferred representatives of the compounds of the formula (I) are the following derivatives:

1-(4-chlorophenyl)-pyrido[2,1-f]-as-triazinium salts, preferably the bromide or the perchlorate, 1-phenyl-pyrido[2,1-f]-as-triazinium salts, preferably the bromide or the perchlorate.

The 1-(4-chlorophenyl)-as-triazino[6,1-a]-isoquinolinium salts, primarily the bromide, possess particularly valuable pharmaceutical properties.

According to a further feature of the present invention there is provided a process for the preparation of the condensed as-triazine derivatives of the formula (I), characterized by a. to prepare a subgroup of the compounds having the formula (I), wherein $R_1$ is oxo, n=1 and $R_2$, $R_3$, $X^-$ and Z have the above defined meanings, $a_1$. cyclizing a compound of the formula (II)

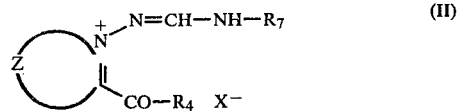

wherein Z and $X^-$ have the above defined meanings, $R_7$ is hydrogen or $C_{1-10}$ alkyl and $R_4$ is a leaving group, or $a_2$. reacting a compound of the formula (III)

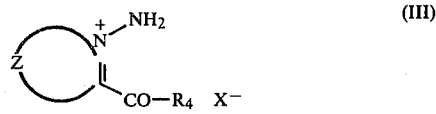

wherein $R_4$, Z and $X^-$ have the same meanings as above, with a compound of the formula (IV)

$$R_5-NH-CO-R_3 \qquad (IV)$$

wherein $R_5$ is hydrogen or $C_{1-10}$ alkyl and $R_3$ has the same meanings as above, in the presence of a dehydrating agent, and cyclizing the compound of the formula (II) thus-obtained; or b. to prepare a subgroup of the compounds having the formula (I), wherein $R_1$ is other than oxo, n is 0 and $R_1'$ and $R_2'$ form together a double bond, $R_3$, Z, n and $X^-$ have the above defined meanings $b_1$. cyclizing a compound of the formula (V)

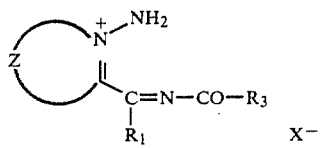

wherein Z, $R_1$, $R_3$ and $X^-$ have the same meanings as above, or $b_2$. reacting a compound of the formula (VI)

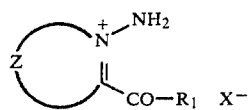

wherein $R_1$, Z and $X^-$ have the above defined meanings, with an amide of the formula (VII)

$$H_2N-CO-R_3 \qquad (VII)$$

wherein $R_3$ has the same meanings as above, in the presence of a dehydrating agent, and cyclizing the compound of the formula (V) thus-obtained, or $b_3$. reacting a compound of the formula (VIII)

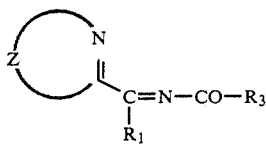

wherein $R_1$, $R_3$ and Z have the same meanings as above, with an O-substituted hydroxylamine and cyclizing the compound of the formula (V) thus-obtained, after or without isolation; or $b_4$. reacting an imide of the formula (IX)

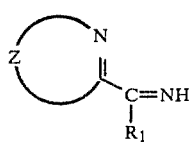

wherein $R_1$ and Z have the same meanings as above, with a carboxylic acid of the formula (X)

$$R_3-COOH \qquad (X)$$

wherein $R_3$ has the above defined meanings, or with a reactive derivative thereof, optionally in the presence of an acid binding agent and cyclizing the compound of the formula (V) thus-obtained after or without isolation; or if desired, introducing a $C_{1-10}$ alkyl or an amino group into the compound of the formula (I) thus-obtained, wherein $R_2$ represents hydrogen, and, if desired, replacing the anion $X^-$ in the compound of the formula (I) by another anion $X^-$.

According to variant (a) of the process according to the invention the compounds of the formula (I), wherein $R_1$ represents an oxo group, n is 1 and $R_2$, $R_3$, $X^-$ and Z have the above defined meanings, are prepared by cyclizing a compound of the formula (II). The cyclization can be performed under heating in the presence of a dehydrating agent. The reaction temperature varies between 60° C. and 120° C. As dehydrating agents, phosphorus halides (e.g. phosphorus oxychloride or phosphorus pentachloride), polyphosphoric acid or dicyclohexylcarbodiimide are preferably used. The phosphorus oxychloride is particularly preferred as dehydrating agent.

The starting substances of the formula (II) can be prepared by reacting an N-amino-α-carboxylic ester of the formula (III) with a compound of the formula (IV). The reaction is preferably carried out at a temperature between 20° C. and 60° C. in the presence of a dehydrating agent. For this purpose the dehydrating agents listed at the cyclization of the compounds of the formula (II) can be used. The reaction is preferably carried out in an organic solvent. As reaction medium any solvent inert under the given circumstances can be used, e.g. halogenated hydrocarbons (such as chloroform, hydrocarbon tetrachlorides, chlorobenzene), aromatic hydrocarbons (e.g. xylene, toluene, benzene), dialkyl amides (e.g. dimethylformamide), dialkyl sulfoxides (e.g. dimethyl sulfoxide, etc.), cyclic ethers tetrahydrofurane, dioxane, aliphatic ethers (e.g. diethyl ether), other hydrocarbons (e.g. hexane, gasoline) acetonitrile, or mixtures thereof.

The leaving group ($R_4$) in the compounds of the formula (III) is preferably a $C_{1-20}$ alkoxy group (such as methoxy, ethoxy, n-propoxy, isopropoxy, hexyloxy, n-decyloxy, n-dodecyloxy, an optionally substituted $C_{6-10}$ aryloxy group (e.g. phenoxy or naphthyloxy) or a $C_{6-10}$ aryl-($C_{1-3}$ alkoxy) group (e.g. benzyloxy, β-phenylethoxy group). The aryl ring of the above mentioned aryloxy and arylalkoxy groups may optionally contain one or more identical or different substituents (such as nitro, amino, $C_{1-6}$ alkoxy, $C_{1-6}$ alkyl, hydroxy or halogen).

The compounds of the formula (II) can be isolated or cyclized without isolation in the same reaction mixture where they have been formed.

When the reaction of the compounds of the formulae (III) and (IV) is carried out at lower temperatures—generally below 60° C.—, the compounds of the formula (II) can be isolated. When the reaction mixture obtained at the reaction of the compounds of the formulae (III) and (IV) is heated to a higher temperature —generally to a temperature of 60° C. to 120° C.—the cyclization of the compounds of the formula (II) is accomplished and directly the desired compounds of the formula (I) are obtained.

According to variant (a) of the process according to the invention compounds of the formula (I), wherein $R_1$ is an oxo group, and n is 1 are obtained. These compounds are pyrido[2,1-f]-as-triazinium-1-one, as-triazino[1,6-a]-quinoxalinium-4-one, as-triazino[6,1-a]- isoquinolinium-1-on, as-triazino[1,6-f]-phenantridinium-1-one salts and the substituted derivatives thereof.

It has been found that different molecules of Zwitterion type can be derived from the above mentioned compounds which can be illustrated by the resonance-structures of the formulae (e), (f) and (g).

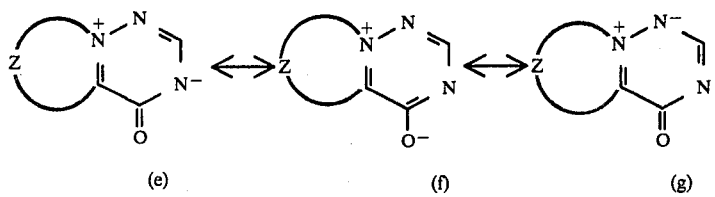

(e) (f) (g)

The invention encompasses the compounds of the general formula (I) corresponding to all the Zwitter-ion structures mentioned above.

According to variant (b) of the process according to the invention a compound of the formula (V) is cyclized. The reaction can be performed by heating the compounds of the formula (V) in the presence of a dehydrating agent. The reaction temperature is preferably between 60° C. and 120° C. As dehydrating agents, the compounds listed at variant (a), (particularly phosphorus oxychloride) are preferably used. By this variant compounds of the formula (I), wherein $R_1$ is other than an oxo group, n is 0 and $R_1'$ and $R_2'$ form together a valency bond are obtained.

The compounds of the formula (V) can be prepared by reacting an oxo compound of the formula (VI) with an amide of the formula (VII). The reaction can be carried out in a solvent, in the presence of a dehydrating agent at a temperature of 20° C. to 60° C. For this purpose the solvents and dehydrating agents listed at variant (a) are preferably used. The compounds of the formula (V) thus-obtained can be isolated or cyclized directly in the same reaction mixture where they have been formed.

When the reaction of the compounds of the formulae (VI) and (VII) is performed at a lower temperature—generally at 20° C. to 60° C.—the compounds of the formula (V) can be isolated. When the reaction is carried out at a higher temperature (e.g. between 60° C. and 120° C.) the compounds of the formula (V) are cyclized immediately, so the desired compounds of the formula (I) are obtained directly.

The compounds of the formula (V) can be prepared also by reacting a compound of the formula (VIII) with an O-substituted hydroxylamine. As O-substituted hydroxylamine preferably O-(p-toluenesulfonyl)-hydroxylamine can be used. The reaction is carried out at room temperature or under heating in an organic solvent. As reaction medium the solvents listed at variant (a) can be used. When the above reaction is performed under mild heating or for a longer time, the compounds of the formula (V) are cyclized spontaneously, without isolation. The cyclization can be quickened by dehydrating agents. For this purpose the dehydrating agents listed at variant (a) are suitable.

The compounds of the formula (VIII) can be prepared by reacting an imide of the formula (IX) with a carboxylic acid of the formula (X) or with a reactive derivative thereof optionally in the presence of an acid binding agent. As reactive derivatives of the carboxylic acids of the formula (X) preferably the corresponding acid halide (e.g. chloride or bromide), acid anhydride, mixed anhydride, ester or imidazolide are used. The reaction is carried out at a temperature between 0° C. and 120° C., preferably at about room temperature. As acid binding agent inorganic bases (e.g. alkali hydroxides, alkali carbonates or alkali bicarbonates) such as sodium or potassium hydroxide, sodium or potassium carbonate or bicarbonate (or organic bases) e.g. triethylamine, trimethylamine, pyridine can be used. If the reaction is performed in the presence of an acid binding agent, the compounds of the formula (VIII) can be isolated.

The above reaction is generally carried out by using an equimolar amount of the reactants or a small excess of one of the reactants dissolved or suspended in a suitable solvent, optionally in the presence of a dehydrating or acid binding agent at a suitable temperature. When the reaction is completed the product usually separates from the reaction mixture. The isolation of the product is carried out by usual methods (e.g. filtration or centrifugation). If desired, the product can be purified.

Into a compound of the formula (I), wherein $R_2$ represents hydrogen, a $C_{1-10}$ alkyl group can optionally be introduced. This reaction can be performed by N-alkylating methods known per se. As alkylating agent the corresponding alkyl halides (e.g. methyl iodide, ethyl iodide) or dialkyl sulfates (e.g. dimethylsulfate or diethylsulfate) or any usual alkylating agent (e.g. diazomethane) can be used. The reaction is preferably carried out in the presence of an acid binding agent. For this purpose inorganic bases (e.g. sodium hydroxide, potassium hydroxide, sodium carbonate, potassium carbonate, sodium bicarbonate, potassium bicarbonate), or organic bases (e.g. trimethylamine, triethylamine or pyridine) can be used. The alkylation is carried out between 20° C. and the boiling point of the reaction mixture, preferably under heating. As reaction medium, suitable inert solvents—preferably the solvents listed at variant (a)—can be used.

Into a compound of the general formula (I) obtained, wherein $R_2$ is hydrogen, an amino group can also be introduced. The reaction can be performed by using an O-substituted hydroxylamine, preferably O-(p-toluenesulfonyl)-hydroxylamine. One proceeds preferably in organic solvent, at room temperature or under mild heating. As reaction medium, the solvents listed at variant (a) can be used.

In a compound of the general formula (I) obtained the anion $X^-$ can, if desired, be replaced by an other anion $X^-$. The reaction is performed by reacting the compound of the general formula (I) with the acid or salt containing the desired anion. The perchlorates of the general formula (I) are prepared by reacting a compound of the general formula (I) containing an other anion (e.g. p-toluenesulfonyl anion) with perchloric acid.

The compounds of the general formula (III) used as starting substances can be prepared by the method of Y. Tamura et al. [Tetrahedron Letters 40, 4133–35 (1972)], the ketimines of the general formula (IX) are produced as described in Compt. Rend. 258, (12) 3323 (1964), and the starting substance of the ketones of the general formula (VI) is prepared by the method described in Liebigs. Ann. Chem. (1976) 1351-6. The other starting substances are known compounds.

The starting substances of the general formula (II) can be prepared by reacting a compound of the general formula (III) with a compound of the general formula (IV) in the presence of a dehydrating agent.

The starting substances of the formula (V) can be prepared as follows:

a. a compound of the formula (IV) is reacted with an amide of the formula (VII) in the presence of a dehydrating agent; or b. a compound of the formula (VIII) is reacted with an O-substituted hydroxylamine; or c. an imide of the formula (IX) is reacted with a carboxylic acid of the formula (IX) or with a reactive derivative thereof optionally in the presence of an acid binding agent, and the imide of the formula (VIII) thus-obtained is reacted with an O-substituted hydroxylamine (in the formulae $R_1$, $R_3$, $R_4$, $R_5$, $R_7$, Z and $X^-$ have the same meanings as above).

The compounds of the formula (I) possess valuable pharmaceutical properties and can advantageously be used in therapy.

The effects of the compounds of the formula (I) are illustrated by the test-results described below. The following derivatives served as test compounds:

Compound A = 1-phenyl-pyrido[2,1-f]-as-triazinium bromide

Compound B = 1-(4-chlorophenyl)-pyrido[2,1-f]-as-triazinium bromide

Compound C = 1-(4-chlorophenyl)-as-triazino[6,1-a]-isoquinolinium bromide

A. Acute toxicity a. On mice

The acute toxicity of the new compounds according to the invention was determined on white mice of both sexes weighing 18-24 g belonging to the strain CFLP. Administration was effected with an oral dosage of 20 ml/kg. After treatment the animals were kept under observation for 4 days. The toxicity data were determined by a graphic method and are given in Table I(a).

TABLE I/a

| Test Compound | $LD_{50}$ mg/kg p.o. |
|---|---|
| A | 1400 |
| B | 900 |
| C | 600 |
| Amitriptylin | 225 | b. On rats

The acute toxicity was investigated also on Wistar rats. A 0.5% suspension prepared from the test compound and carboxymethylcellulose was administered orally to the animals. The results are given in Table I(b).

TABLE I/b

| Test compound | $LD_{50}$ mg/kg p.o. |
|---|---|
| C | 1000 |
| Amitriptylin | 530 |

B. Tetrabenazine antagonism a. On mice

Groups of animals consisting of 10-20 mice each were examined. A 0.9% sodium chloride solution was administered to the mice of the control group in a dosage of 20 ml/kg. After 30 minutes 50 mg/kg of tetrabenazine were administered. The animals with closed interpalpebral zone were counted 30, 60, 90 and 120 minutes after the administration of the tetrabenazine. The data were summarized and the inhibition in comparison with the control was determined. The results are given in Table II(a).

TABLE II/a

| Test compound | $ED_{50}$ mg/kg (p.o.) | Therapeutic index $LD_{50}/ED_{50}$ |
|---|---|---|
| A | 30 | 46.7 |
| B | 14.0 | 64.2 |
| C | 3.2 | 187.5 |
| Amitriptylin | 12 | 18.75 | b. On rats

The experiments were carried out on the analogy of the tests described at point (a). The results are given in Table II(b).

TABLE II/b

| Test compound | Tetrabenazine ptosis ant. $ED_{50}$ mg/kg | Therapeutic index | Reserpine-ethanol narcose ant. $ED_{50}$ mg/kg | Ther. index |
|---|---|---|---|---|
| C | 5.6 | 178.6 | 40.0 | 25.0 |
| Amitriptylin | 11.5 | 46.1 | 40.0 | 13.25 |

C. Potentiation of yohimbine toxicity on mice

The experiments were carried out by the method of Quinton et al. The test compound was administered orally in a volume of 20 ml/kg half an hour before the administration of the standard yohimbine dose. The results are given in Table III.

TABLE III

| Test compound | $ED_{50}$ mg/kg (p.o.) | Therapeutic index $LD_{50}/ED_{50}$ |
|---|---|---|
| A | 66.0 | 21.2 |
| B | 50.0 | 18.0 |
| C | 3.5 | 171.4 |

As the results of the above Tables show the new compounds according to the invention exert antidepressant effect far exceeding that of the excellent commercial antidepressant Amitriptylin.

According to a further feature of the present invention there are provided pharmaceutical compositions containing as active agent a compound of the formula (I) together with an appropriate inert, solid or liquid pharmaceutical carrier. These compositions can be prepared in solid (e.g. in tablets, capsules, suppositories, etc.) or in liquid forms (e.g. solutions, suspensions, emulsions, etc.). The compositions can be administered orally or parenterally.

As carriers solid diluents or fillers, sterile aqueous media or non-toxic organic solvents can be used. The tablets intended for oral use may contain sweeteners or other additives. The pharmaceutical compositions according to the invention generally contain 0.1-90% by weight of an ingredient of the formula (I). The tablets may contain further additives (e.g. sodium citrate, calcium carbonate, dicalcium phosphate), different auxiliaries (e.g. starch, preferably potato starch), binders (e.g. polyvinyl pyrrolidone or gelatin) or lubricants (e.g. magnesium stearate, sodium laurylsulfate or talc). For the preparation of aqueous suspensions and/or elixirs intended for oral use the active ingredient of the formula (I) may be admixed with different emulgeants and/or dilutents /e.g. water, ethanol, propylene glycol, glycerine, flavoring and coloring agents.

For parenteral use the solution of the active ingredient of the general formula (I) in sesame oil, peanut oil, aqueous propylene glycol, N,N-dimethylformamide or in other pharmaceutically acceptable solvents—or, in case of a water-soluble active ingredient, the sterile aqueous solution—can be used.

If necessary, the aqueous solutions can be buffered in the usual way, or isotonic solutions can be prepared, e.g. with the aid of sodium chloride or glucose. The aqueous solutions thus obtained can be used for the preparation of intravenous, intramuscular and intraperitoneal injections. The sterile aqueous solutions can be prepared by known methods.

The pharmaceutical compositions according to the invention can be prepared by known methods generally applied in the pharmaceutical industry.

The daily oral dose of the compounds of the formula (I) amounts approximately to about 0.01–10 mg. These values are, however, nearly of an informative character and the actually applied dose depends on the circumstances of the given case and the prescriptions of the physician and may lay below or above the said range.

The invention is illustrated by the following Examples of non-limiting character:

EXAMPLE 1

Preparation of 1-phenyl-pyrido[2,1-f]-as-triazinium perchlorate

To a solution of 0.18 g (0.5 millimoles) of 1-amino-2-benzoyl-pyridinium-p-toluene sulfonate in 50 ml of formamide 3.35 g (22 millimoles) of phosphorus oxychloride are added. The reaction mixture is allowed to stand for an hour then poured onto ice, 1 ml of 70% perchloric acid is added and the mixture is extracted with nitromethane. After evaporating the solvent 120 mg of desired compound are obtained.

Yield: 80%

M.p.: 259°–260° C.

Analysis: Calculated: N%=13.66; Cl%=11.52. Found: N%=13.62; Cl%=11.52.

The above compound is converted into 1-phenyl-pyrido-[2,1-f]-as-triazinium bromide as described in paragraph 2 of Example 5.

M.p.: 271°–272° C.

The starting substance is prepared as follows: To a solution of 1 g (5.5 millimoles) of 2-benzoyl-pyridine in 10 ml of dichloromethane a solution of 1.04 g (5.5 millimoles) of O-(p-toluenesulfonyl)-hydroxylamine in 20 ml of dichloromethane is added. The reaction mixture is allowed to stand for 2 hours, then ether is added. 1.5 g (74%), of 1-amino-2-benzoyl-pyridinium-p-toluene sulfonate are obtained.

M.p.: 146°–147° C.

Analysis: Calculated: N%=7.56; S%=8.66. Found: N%=7.66; S%=8.73.

EXAMPLE 2

Preparation of 1-phenyl-3-methyl-pyrido[2,1-f]-as-triazinium perchlorate

To a solution of 0.3 g (1.34 millimoles) of phenyl-2-pyridyl-(N-acetyl)-ketimine in dichloromethane a solution of 0.25 g (1.34 millimoles) of O-(p-toluenesulfonyl)-hydroxylamine in 20 ml of dichloroethane is added, and the reaction mixture is stirred at room temperature for 2 hours. To obtain the desired compound the reaction mixture is treated as described in Example 1. 0.21 g of 1-phenyl-3-methyl-pyrido[2,1-f]-as-triazinium perchlorate are obtained.

M.p.: 261°–262° C. (from a mixture of nitromethane and ethanol).

Yield: 46.6%.

Analysis: Calculated: N%=13.06; Cl%=11.02. Found: N%=13.02; Cl%=11.05.

The starting substance is prepared as follows: To a solution of 1.5 g (8.25 millimoles) of phenyl-2-pyridylketimine in 7 ml of benzene 0.84 g (8.3 millimoles) of triethylamine and 0.65 g (8.35 millimoles) of acetyl chloride are added. The reaction mixture is allowed to stand at room temperature then the triethyl-ammonium chloride and the solvent are removed. 1.4 g (75.5%) of phenyl-2-pyridyl-(N-acetyl)-ketimine are obtained.

M.p.: 85°–86° C. (from ether).

Analysis: Calculated: N%=12.49. Found: N%=12.50.

EXAMPLE 3

Preparation of 1-oxo-pyrido[2,1-f]-as-triazinium perchlorate 21.2 g (0.0825 moles) of 1-(N-formamidino)-2-carbethoxy-pyridinium perchlorate are dissolved in 100 ml of phosphorus oxychloride and the mixture is boiled for half an hour. Then it is evaporated and the residue is crystallized from ethanol. 16.7 g of desired compound are obtained.

Yield: 82%.

M.p.: 243°–244° C. (from mixture of ethanol and water).

Analysis: Calculated: N%=16.97 Cl%=14.32. Found: N%=16.78 Cl%=14.21.

The starting substance is prepared as follows: 30 g (0.198 moles) of pyridine-2-ethyl-carboxylate are dissolved in dichloromethane and a solution of 37 g (0.198 moles) of O-(p-toluenesulfonyl)-hydroxylamine in dichloromethane is added. The reaction mixture is stirred at room temperature for an hour then cooled and allowed to stand overnight in a refrigerator. After evaporating the solvent the residue thus-obtained is dissolved in water, the solution is saturated with sodium perchlorate, extracted with nitromethane and the solvent is removed. 42.4 g (80%) of 1-amino-2-carbethoxy-pyridinium perchlorate are obtained.

M.p.: 121°–122° C.

Analysis: Calculated: N%=10.51. Found: N%=10.50.

0.27 g (1 millimole) of 1-amino-2-carbethoxy-pyridinium perchlorate are dissolved in formamide, then 0.4 ml of phosphorus oxychloride are added. The reaction mixture is stirred at 60° C. for 30 minutes then dissolved in water, extracted with nitromethane and the solvent is removed. 0.15 g (52%) of 1-(N-formamidino)-2-carbethoxy-pyridinium perchlorate are obtained.

M.p.: 116°–117° C. (from mixture of ethanol and ether).

Analysis: Calculated: N%=14.31; Cl%=12.07. Found: N%=14.20; Cl%=12.12.

EXAMPLE 4

Preparation of 1-(4-chlorophenyl)-as-triazino[1.6-b]-isoquinolinium perchlorate 100 mg of 2-amino-3-(4-chlorobenzoyl)-isoquinolinium-p-toluene sulfonate (0.23 moles) are suspended in 1.5 ml of phosphorus oxychloride, 0.5 ml of formamide are added and the mixture is stirred at 80° C. for 30 minutes. Thereafter it is poured onto icy water and treated with perchloric acid. 54 mg of desired compound are obtained.

Yield: 62%.
M.p.: 203°–204° C.
Analysis: Calculated: N%=10.71. Found: N%=10.48.

The starting substance is prepared as follows: To a mixture of 0.62 g (26 millimoles) of metallic magnesium and 8 ml of anhydrous ether a solution of 5.0 g (26 millimoles) of 4-chloro-bromobenzene in ether is dropwise added, the Grignard solution thus-obtained is admixed with 3.1 g (20 millimoles) of 3-cyano-isoquinoline, and the reaction mixture is stirred at room temperature for an hour. The Grignard complex is decomposed with an ammonium chloride solution, the solvent is distilled off and the residue is recrystallized from ethanol. 3.2 g (60%) of 3-(4-chlorobenzoyl)-isoquinoline imine are obtained.

M.p.: 151°–152° C.
Analysis: Calculated: N%=10.50. Found: N%=10.38.

The ketimine prepared according to the above paragraph is treated with 20 ml of concentrated hydrochloric acid, the reaction mixture is made alkaline with sodium hydroxide and the solvent is distilled off. 3.1 g (95%) of 3-(4-chlorobenzoyl)-isoquinoline are obtained.

M.p.: 126°–127° C.
Analysis: Calculated: N%=5.24. Found: N%=5.19.

5 g (19 millimoles) of 3-(4-chlorobenzoyl)-isoquinoline are dissolved in 10 ml of dichloromethane, then 4 g (22 millimoles) of O-(p-toluenesulfonyl)-hydroxylamine are added, and the mixture is allowed to stand for an hour. 6 g (73%) of 2-amino-3-(4-chlorobenzoyl)-isoquinolinium-p-toluene sulfonate are obtained.

M.p.: 201°–202° C.
Analysis: Calculated: S%=7.05. Found: S%=7.15.

EXAMPLE 5

Preparation of 1-(4-chlorophenyl)-as-triazino[6,1a]-isoquinolinium bromide

One proceeds as described in Example 1, with the difference that 2-amino-1-(4-chlorobenzoyl)-isoquinolinium-p-toluene sulfonate is used instead of 1-amino-2-benzoylpyridinium-p-toluene sulfonate. The 1-(4-chlorophenyl)-as-triazino[6.1-a]-isoquinolinium perchlorate is obtained with a yield of 70%.

M.p.: 243°–244° C. (from acetonitrile).

6.9 g (17.5 millimoles) of the above compound is dissolved in acetonitrile and reacted with 5.5 g (30 millimoles) of triethyl-ammonium bromide. 4.1 g of desired compound are obtained.

M.p.: 271°–272° C.

Yield: 62.6%.
Analysis: Calculated: N%=11.28; Cl%=19.03. Found: N%=11.18; Cl%=18.98.

The starting substance is prepared as follows:

To a solution of 3.1 g (20 millimoles) of 1-cyanoisoquinoline in anhydrous ether a Grignard reagent prepared from 5.75 g (30 millimoles) of 4-chloro-bromobenzene and 0.735 g (30 millimoles) of magnesium metal is added. The reaction mixture is allowed to stand for a night, thereafter the complex is decomposed with ammonium chloride solution, acidified with a 20% sulfuric acid and allowed to stand for 2 hours. After neutralization the ether phase is separated and the solvent is distilled off. 4.1 g (76.6%) of 1-(4-chlorobenzoyl)-isoquinoline are obtained.

M.p.: 100°–101° C.
Analysis: Calculated: N%=6.44. Found: N%=6.46.

The 1-(4-chlorobenzoyl)-isoquinoline prepared as described above is reacted with O-(p-toluenesulfonyl)-hydroxylamine as described in paragraph 3 of Example 1. The 2-amino-1-(4-chlorobenzoyl)-isoquinolinium-p-toluene sulfonate is obtained with a yield of 88.5%.

M.p.: 189°–190° C. (from the mixture of nitromethane and ether).

Analysis: Calculated: N%=6.16; Cl%=7.79. Found: N%=6.18; Cl%=7.56.

EXAMPLE 6

Preparation of 1-(4-chlorophenyl)-pyrido[2,1-f]-as-triazinium perchlorate

One proceeds as described in Example 1, with the difference that 1-amino-2-(4-chlorobenzoyl)-pyridinium-p-toluene sulfonate is used as starting substance. The desired compound is obtained with a yield of 79.5%.

M.p.: 249°–250° C.
Analysis: Calculated: N%=12.28; Cl%=20.73. Found: N%=12.23; Cl%=20.45.

The above compound is converted into 1-(4-chlorophenyl)-pyrido[2,1-f]-as-triazinium bromide as described in paragraph 2 of Example 5.

The starting substance is prepared as described in paragraph 2 of Example 1, with the difference that 2-(4-chlorobenzoyl)-pyridine is used instead of 2-benzoyl-pyridine. The 1-amino-2-(4-chlorobenzoyl)-pyridinium-p-toluene sulfonate is obtained with a yield of 89%.

M.p.: 151°–152° C.

EXAMPLE 7

Preparation of 2-methyl-1-oxo-pyrido[2,1-f]-as-triazinium iodide 6.0 g (0.024 moles) of 1-oxo-pyrido[2,1-f]-as-triazinium perchlorate are boiled in acetonitrile in the presence of 6 ml of methyl iodide and 3.4 ml of triethylamine for an hour. 5.6 g of desired compound are obtained.

Yield: 80%.
M.p: 273°–274° C. (from a mixture of ethanol and water).

Analysis: Calculated: N%=14.54; I%=43.90. Found: N%=14.62; I%=44.20.

EXAMPLE 8

Preparation of 2-methyl-1-oxo-pyrido[2,1-f]-as-triazinium perchlorate 1.3 g (4.9 millimoles) of 1-amino-2-carbethoxy-pyridinium perchlorate are dissolved in 3 ml of N-methyl-formamide, then 2 ml of phosphorus oxychloride are added and the mixture is reacted at 80° C. for an hour. Then it is poured onto ice and treated with sodium perchlorate. 1.1 g (86.7%) of desired compound are obtained.

M.p.: 284°–285° C.

Analysis: Calculated: N% = 16.06; Cl% = 13.55. Found: N% = 15.98; Cl% = 13.72.

EXAMPLE 9

Preparation of 2,3-dimethyl-1-oxo-pyrido[2,1-f]-as-triazinium bromide

To a solution of 12 g (45 millimoles) of 1-amino-2-carbethoxy-pyridinium perchlorate in 25 ml of N-methyl-acetamide 20 ml of phosphorus oxychloride are added at 90° C. The reaction mixture is allowed to stand for an hour, thereafter poured onto ice, the aqueous solution is saturated with sodium perchlorate and the separated product is filtered off. 10.3 g (83%) of 2,3-dimethyl-1-oxo-pyrido[2,1-f]-as-triazinium perchlorate are obtained.

M.p.: 270°–271° C. (from a mixture of ethanol and water).

The product thus-obtained is converted into the desired compound as described in Example 5.

Yield: 93%.

M.p.: 256°–257° C. (from a mixture of ethanol and water).

Analysis: Calculated: Br% = 31.20. Found: Br% = 31.31.

EXAMPLE 10

Preparation of 4-(4-chlorophenyl)-as-triazino[1,6-a]-quinolinium perchlorate A mixture of 0.5 g (1.1 millimoles) of 1-amino-2-(4-chlorobenzoyl)-quinolinium-p-toluene sulfonate, 3 ml of formamide and 2 ml of phosphorus oxychloride is stirred at 90° C. for an hour. Thereafter it is poured into water, treated with perchloric acid, and the separated product is filtered off. 0.33 g of desired compound are obtained.

Yield: 77%.

M.p.: 193°–194° C.

Analysis: Calculated: N% = 10.71. Found: N% = 10.52.

The starting substance is prepared as follows: 15.4 g (0.1 mole) of 2-cyano-quinoline are dissolved in 200 ml of anhydrous ether, and a Grignard reagent prepared from 2.5 g (0.13 moles) of 4-chloro-bromobenzene and 3.16 g (0.13 moles) of magnesium metal are added. The reaction mixture is allowed to stand overnight, thereafter it is poured into a mixture of 15 g of ammonium bromide and ice, acidified with sulfuric acid and the organic phase is separated. After evaporating the ether the product thus-obtained (24 g) is recrystallized from ethanol. The 2-(4-chlorobenzoyl)-quinoline is obtained with a yield of 89%.

M.p.: 130°–131° C.

Analysis: Calculated N% = 5.23. Found: N% = 5.21.

1.43 g (0.53 millimoles) of 2-(4-chlorobenzoyl)-quinoline dissolved in 20 ml of dichloromethane are reacted with 1 g (0.53 millimoles) of O-(p-toluenesulfonyl)-hydroxylamine at 20° C. The separated product is filtered off. 1.4 g of 1-amino-2-(4-chlorobenzoyl)-quinoxalinium-p-toluene sulfonate are obtained.

Yield: 58%.

M.p.: 219°–220° C.

Analysis: Calculated: N% = 6.16. Found: N% = 6.08.

What we claim is:

1. A pharmaceutically acceptable salt of the formula (I)

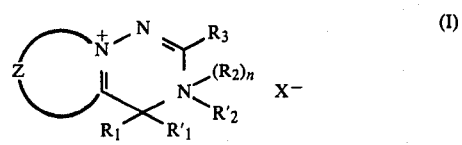

wherein

Z is a buta-1,3-dienyl group of the formula

or a group of the formula

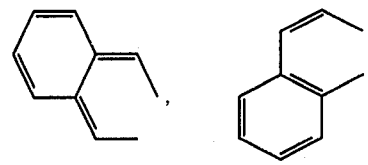

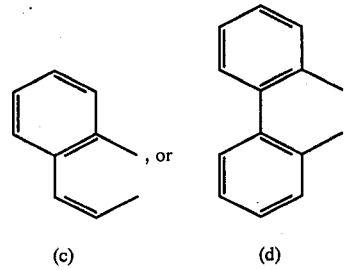

$R_1$ is phenyl, halophenyl, or oxo;

$R_2$ is hydrogen or $C_1$ to $C_4$ alkyl;

$R_3$ is hydrogen or $C_1$ to $C_4$ alkyl;

$X^-$ is a halide, perchlorate, p-toluene-sulfonate or methanesulfonate ion; and in the case where $R_1$ is oxo, $R_1'$ and $R_2'$ represent nothing and n is 1; and in the case where $R_1$ is other than oxo, $R_1'$ and $R_2'$ form an additional bond between the carbon and nitrogen atoms, and n is 0.

2. The salt defined in claim 1 wherein Z is

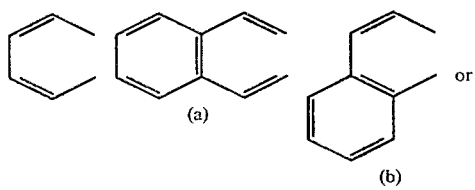

and X⁻ is a chloride, perchlorate, bromide or p-toluenesulfonate ion.

3. The salt defined in claim 1 wherein $R_1$ is phenyl or halophenyl.

4. The salt defined in claim 1 wherein $R_1$ is phenyl.

5. A 1-(4-chlorophenyl)-as-triazino-(6,1-a)-isoquinolinium salt as defined in claim 1.

6. A 1-(4-chlorophenyl)-as-triazino-(6,1-a)-isoquinolinium bromide as defined in claim 1.

7. A 1-(4-chlorophenyl)-pyrido(2,1-f)-as-triazinium salt as defined in claim 1.

8. A 1-phenyl-pyrido(2,1-f)-as-triazinium salt as defined in claim 1.

9. An antidepressant composition which comprises as active ingredient an antidepressant effective amount of the salt defined in claim 1 together with a suitable solid or liquid inert pharmaceutical carrier.

10. A method of treating depression in an animal subject which comprises the step of orally administering to said animal subject an anti-depressant effective amount of the salt defined in claim 1.

* * * * *